United States Patent
Ma et al.

(10) Patent No.: US 11,453,638 B2
(45) Date of Patent: Sep. 27, 2022

(54) PROCESS METHOD FOR PRODUCING PESTICIDE BY USING CARBON DIOXIDE

(71) Applicant: Nankai University, Tianjin (CN)

(72) Inventors: Jiangong Ma, Tianjin (CN); Zhiqiang Wang, Tianjin (CN); Peng Cheng, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 0 days.

(21) Appl. No.: 17/253,192

(22) PCT Filed: Oct. 21, 2019

(86) PCT No.: PCT/CN2019/112155
§ 371 (c)(1),
(2) Date: Dec. 17, 2020

(87) PCT Pub. No.: WO2020/098450
PCT Pub. Date: May 22, 2020

(65) Prior Publication Data
US 2021/0269390 A1  Sep. 2, 2021

(30) Foreign Application Priority Data
Nov. 15, 2018  (CN) .......................... 201811356383.0

(51) Int. Cl.
*C07C 231/12* (2006.01)
*C07C 51/15* (2006.01)
(Continued)

(52) U.S. Cl.
CPC ............ *C07C 231/12* (2013.01); *A01N 37/22* (2013.01); *B01J 23/04* (2013.01); *B01J 23/72* (2013.01);
(Continued)

(58) Field of Classification Search
None
See application file for complete search history.

(56) References Cited

U.S. PATENT DOCUMENTS 3,782,918 A    1/1974  Walworth
3,801,630 A *  4/1974  Diehl .................... C07C 233/00
                                                  564/123
(Continued)

FOREIGN PATENT DOCUMENTS

WO    2004062723    7/2004

OTHER PUBLICATIONS

Wikipedia entry for "Schlenk flask": https://en.wikipedia.org/wiki/Schlenk_flask, downloaded on Nov. 3, 2021 (Year: 2021).*

(Continued)

*Primary Examiner* — Amy C Bonaparte
(74) *Attorney, Agent, or Firm* — Andrew C. Cheng

(57) ABSTRACT

A process method for producing a pesticide by using carbon dioxide includes: weighing a 1,3-cyclohexanedione substrate 1(a-e), a catalyst and $Cs_2CO_3$ in a Schlenk bottle, degassing, and continuously introducing 1 atm of carbon dioxide; adding a solvent and reacting for 48 h in an oil bath at 50° C. After the reaction was completed, post-treatment was carried out to obtain a 2-carboxyl-1,3-cyclohexanedione compound 2(a-e). The obtained acid is acylated and then added dropwise to a dichloromethane solution containing aniline to react for 2 h at room temperature. After the reaction, column chromatography was performed to obtain a pesticide compound 3(a-e). Adding the pesticide compound 3(a-e) into 50% concentrated sulfuric acid and refluxing at 80° C. for 8 hours. Through separation, a pesticide product compound 4(a-e) was obtained. The process method is simple, with low requirements on equipment, wide (Continued)

sources of raw materials, low cost, low toxicity and easy industrial scale-up production.

3 Claims, 1 Drawing Sheet

(51) Int. Cl.
    *C07C 231/02*     (2006.01)
    *C07C 231/14*     (2006.01)
    *A01N 37/22*     (2006.01)
    *B01J 23/04*     (2006.01)
    *B01J 23/72*     (2006.01)

(52) U.S. Cl.
    CPC ............ *C07C 51/15* (2013.01); *C07C 231/02* (2013.01); *C07C 231/14* (2013.01)

(56) References Cited

U.S. PATENT DOCUMENTS 3,976,785 A     8/1976   Diehl et al.
2009/0264414 A1   10/2009   Andersen et al.

OTHER PUBLICATIONS

Matsumura ("Carboxylation of active methylene compounds with base-magnesium chloride-carbon dioxide mixtures" Nippon Kagaku Kaishi, 1977, p. 1344-8, abstract and list of CAS indexed reactions only) (Year: 1977).*

Weiyang Dai et al., "Synthesis, Structure-activity Relationship Studies and ADMET Properties of 3-aminocyclohex-2-en-1-ones as Chemokine Receptor 2 (CXCR2) Antagonists", ChemMedChem, Feb. 28, 2018.

Ivo Jirkovsky, "Studies on Enaminoketones", Canadian Journal of Chemistry, (Jan. 15, 1974).

* cited by examiner

PROCESS METHOD FOR PRODUCING PESTICIDE BY USING CARBON DIOXIDE

FIELD OF THE INVENTION

The invention belongs to the technical field of utilization of carbon dioxide and preparation of pesticides, relates to a preparation process for producing pesticides by using carbon dioxide, and in particular relates to a process method for generating 2-carboxyl-1-carbonyl-3-hydroxyl-cyclohexane through addition reaction of a 1, 3-cyclohexanedione compound and carbon dioxide in an N, N-dimethylformamide solution. And the obtained acid is further utilized to synthesize a new type of pesticide with high efficiency and potential application, and another type of cyclohexanedione pesticide can be obtained through aniline removal reaction.

BACKGROUND OF THE INVENTION

Carbon dioxide itself is a by-product of combustion, respiration and industrial waste emissions, and it is a non-toxic and harmless gas for a proper amount of carbon dioxide. However, excessive carbon dioxide emissions have aggravated the environmental problems and increased the global temperature. This is a kind of harm that cannot be ignored. The temperature on the earth's surface has been in a relatively stable state. Due to the temperature rise caused by carbon dioxide, a large number of glaciers stored for hundreds of millions of years have accelerated melting, with unimaginable consequences. However, the development of human beings cannot be delayed due to the emission of carbon dioxide. Therefore, a large number of scientific researchers have invested in the conversion and utilization of carbon dioxide so that carbon dioxide will not pose a threat on the premise of ensuring industrial development.

Insecticides, as an indispensable key link in modern agriculture, have been widely used all over the world. At the same time, there are countless agricultural economic losses caused by pests in history. Therefore, pesticide production is the top priority of national development. With the progress of modern industry and science and technology, there are more and more means and methods to control pests and diseases. More and more new pesticides have been continuously developed, which has brought about great improvement in agricultural production and income. However, there is also a problem that cannot be ignored, that is, the existence of drug resistance. Many very famous pesticides, such as organochlorine and organophosphorus, have strong insecticidal activity. However, on the one hand, these famous organic pesticides have formed strong drug resistance in a large number of pests due to their strong toxicity and serious pollution from industrial production. On the other hand, these popular pesticides in those years have withdrawn from the stage of history. Therefore, it is an important strategy to develop new pesticides and improve the synthetic route of existing pesticides.

At present, the industrial production of pesticides has the following disadvantages: (1) High toxicity. (2) High pollution. (3) There are fewer and fewer kinds of new pesticides. (4) There are many by-products.

Therefore, how to prepare and develop new pesticides in a more environmentally friendly way has become a key project for the vast number of scientific researchers.

SUMMARY OF THE INVENTION

The invention aims at the problems of high toxicity and high pollution existing in the prior art, and aims at finding new pesticides, and provides a method for producing pesticide compound 3(3a-3e) by using carbon dioxide and pesticide compound 4(4a-4e) by using pesticide compound 3(3a-3e) under normal temperature and normal pressure. The invention has the advantages of simple operation, lower requirements on equipment, wide raw material sources, low cost, low toxicity, simple treatment, mild synthesis conditions, higher yield, easy industrial amplification, and realization of more efficient and environment-friendly pesticide preparation.

The technical scheme of the invention is as follows:

Technical Scheme 1: A Process for Producing a Pesticide Compound 3(a-e) Using Carbon Dioxide.

The preparation process of the pesticide compound 3(a-e) is shown in FIG. 1 and comprises the following steps:

1) weighing a 1,3-cyclohexanedione substrate 1(a-e), a monovalent copper salt catalyst and cesium carbonate in a Schleck bottle; vacuumizing the Schlenk bottle and introducing carbon dioxide to fill the Schlenk bottle with carbon dioxide gas; then injecting an anhydrous N, N-dimethylformanide (DMF) solvent into the Schlenk bottle, placing the Schlenk bottle into an oil bath set at a temperature of between 50-60° C., and leaving the mixture in the Schlenk bottle to react for 36-48 h; wherein the dosage ratio of 1,3-cyclohexanedione:cesium carbonate:monovalent copper salt catalyst:solvent is 1 mmol: 1.5 mmol: 0.1 mmol: 5 mL;

2) after the reaction is completed, acidifying the resulting mixture with hydrochloric acid, extracting the acidified mixture, and then passing the extracted mixture through a silica gel column to obtain a pure intermediate 2-carboxyl-1,3-cyclohexanedione compound 2(a-e), wherein the recovery yield is at least 80%;

3) adding the 2-carboxyl-1,3-cyclohexanedione compound 2(a-e) obtained in the step 2), thionyl chloride, a tetrahydrofuran solvent and a drop of DMF into a round bottom flask, reacting for 1-2 h in an oil bath at 60-65° C., and removing the solvent from the resulting mixture in the round bottom flask under reduced pressure to obtain an oily yellow liquid, wherein the dosage ratio of the 2-carboxyl-1,3-cyclohexanedione compound:thionyl chloride:tetrahydrofuran solvent is 1 mmol: 2.2 mmol: 10 mL;

4) dropping the oily yellow liquid obtained in step 3) into a dichloromethane solution containing aniline, reacting for 2-3 h at room temperature, obtaining a crude product after the reaction, and separating the crude product by column chromatography to obtain a pesticide compound 3(a-e).

Wherein the monovalent copper salt catalyst is cuprous iodide, cuprous bromide or cuprous oxide.

R in the structural formula of compound 1(a-e) is hydrogen, methyl, dimethyl, ethyl and propyl respectively.

Technical Scheme 2: A Process for Producing a Pesticide product Compound 4(a-e) Using Carbon Dioxide.

On the basis of technical scheme 1, the pesticide product compound 4(a-e) can be obtained through the following steps:

5) adding the pesticide compound 3(a-e) (shown in FIG. 2) obtained in the technical scheme 1 into concentrated sulfuric acid with a mass concentration of 50%, and refluxing at 80° C. for 12 h to produce a crude product which is then purified using a silica gel column to produce a pure pesticide product compound 4(a-e).

The invention has the advantages and beneficial effects that:

The preparation method is simple, the raw material cost is low, the transportation is easy, and the industrial scale-up production is easy. In the insecticidal agent prepared by the method, 3a has a 100% lethal rate to armyworm at a concentration of 600 ppm, 3d has a 100% lethal rate to armyworm at a concentration of 200 ppm, simultaneously has a 100% lethal rate to cotton bollworm and *Ostrinia nubilalis* Hubner at a concentration of 600 ppm, and 3e has a 100% lethal rate to *Culex pipiens* larvae at a concentration of 10 ppm.

DETAILED DESCRIPTION OF THE INVENTION

Embodiment 1

Figure 1:
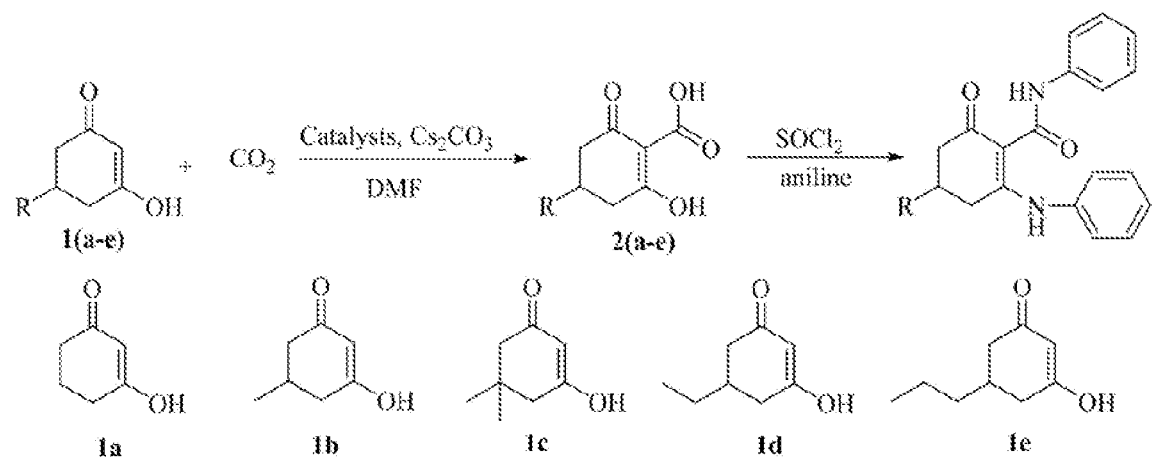
FIG. 1 is a preparation route of technical scheme 1, and various substituents represented by r are given. 1a-1e mentioned in the specification correspond to the substituents of r in structural formulas 1a-1e in FIG. 1.

The invention relates to a process method for producing an insecticide by using carbon dioxide, wherein the insecticide is compound 3(3a-3e), and the preparation process comprises the following steps:

1) Weighing 1 mmol of 1,3-cyclohexanedione compound 1a, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N,N-dimethylformamide, heating to 50° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2a is obtained.

4) Weigh 1 mmol of 2-carboxyl-1,3-cyclohexanedione compound 2a into around bottom flask, add 10 mL of tetrahydrofuran, add 2.2 times equivalent of thionyl chloride, add a drop of DMF, heat to 65° C. and stir for 1 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3a is obtained, and the structural formula is shown in FIG. 1.

Embodiment 2

The invention relates to a process method for producing an insecticide by using carbon dioxide, wherein the insecticide is compound 4a, and the preparation process comprises the following steps:

1) Weigh 3a 100 mg of the compound prepared in embodiment 1 into a round bottom flask, add 6 mL of 50% sulfuric acid, heat to 80° C. and stir for 12 h.

Figure 2:
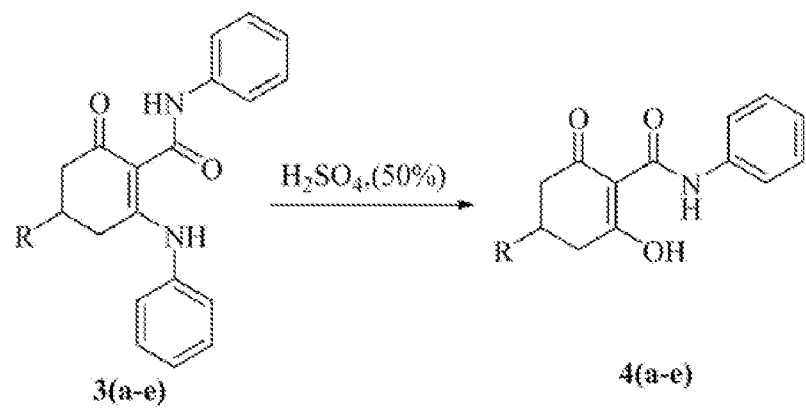
FIG. 2 is the preparation route of technical scheme 2, and R corresponds to 1a-1e in FIG. 1.

2) After completion of the reaction, cool to room temperature, add 50 mL of water to the reaction solution, extract with dichloromethane (3*20 mL), dry with anhydrous magnesium sulfate, filter, and separate by column chromatography (dichloromethane:methanol=10:1). The pure target pesticide compound 4a is obtained, and the structural formula is shown in FIG. 2, wherein r is hydrogen.

Embodiment 3

The invention relates to a process method for producing an insecticide by using carbon dioxide, wherein the insecticide is compound 3b, and the preparation process comprises the following steps:

1) Weighing 1 mmol of 1,3-cyclohexanedione compound 1b, 1.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 50° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2b is obtained.

4) Weigh 1 mmol of 2-carboxyl-1,3-cyclohexanedione compound 2b into a round bottom flask, add 10 mL of tetrahydrofuran, add 2.2 times equivalent of thionyl chloride, add a drop of DMF, heat to 65° C. and stir for 1 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3b is obtained, and the structural formula is shown in FIG. 1.

Embodiment 4

The invention relates to a process method for producing an insecticide by using carbon dioxide, wherein the insecticide is compound 4b, and the preparation process comprises the following steps:

1) Weigh 3b100 mg of the compound prepared in embodiment 1 into a round bottom flask, add 6 mL of 50% sulfuric acid, heat to 80° C. and stir for 12 h.

2) After completion of the reaction, cool to room temperature, add 50 mL of water to the reaction solution, extract with dichloromethane (3*20 mL), dry with anhydrous magnesium sulfate, filter, and separate by column chromatography (dichloromethane:methanol=10:1). The pure target pesticide compound 4b is obtained, and the structural formula is shown in FIG. 2, wherein R is methyl.

Embodiment 5

The invention relates to a process method for producing an insecticide by using carbon dioxide, wherein the insecticide is compound 3c, and the preparation process comprises the following steps:

1) Weighing 1 mmol of 1,3-cyclohexanedione compound 1c, 1.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 50° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2c is obtained.

4) Weigh 1 mmol of 2-carboxyl-1,3-cyclohexanedione compound 2c into a round bottom flask, add 10 mL of tetrahydrofuran, add 2.2 times equivalent of thionyl chloride, add a drop of DMF, heat to 65° C. and stir for 1 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3c is obtained, and the structural formula is shown in FIG. 1.

Embodiment 6

The invention relates to a process method for producing an insecticide by using carbon dioxide, wherein the insecticide is compound 4c, and the preparation process comprises the following steps:

1) Weigh 3c 100 mg of the compound prepared in embodiment 1 into a round bottom flask, add 6 mL of 50% sulfuric acid, heat to 80° C. and stir for 12 h.

2) After completion of the reaction, cool to room temperature, add 50 mL of water to the reaction solution, extract with dichloromethane (3*20 mL), dry with anhydrous magnesium sulfate, filter, and separate by column chromatography (dichloromethane:methanol=10:1). The pure target pesticide compound 4c is obtained, and the structural formula is shown in FIG. 2, wherein R is dimethyl.

Embodiment 7

The invention relates to a process method for producing an insecticide by using carbon dioxide, wherein the insecticide is compound 3d, and the preparation process comprises the following steps:

1) Weighing 1 mmol of 1,3-cyclohexanedione compound 1d, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N,N-dimethylformamide, heating to 50° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2d is obtained.

4) Weigh 1 mmol of 2-carboxyl-1,3-cyclohexanedione compound 2d into a round bottom flask, add 10 mL of tetrahydrofuran, add 2.2 times equivalent of thionyl chloride, add a drop of DMF, heat to 65° C. and stir for 1 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3d is obtained, and the structural formula is shown in FIG. 1.

Embodiment 8

The invention relates to a process method for producing an insecticide by using carbon dioxide, wherein the insecticide is compound 4d, and the preparation process comprises the following steps:

1) Weigh 3d 100 mg of the compound prepared in embodiment 1 into a round bottom flask, add 6 mL of 50% sulfuric acid, heat to 80° C. and stir for 12 h.

2) After completion of the reaction, cool to room temperature, add 50 mL of water to the reaction solution, extract with dichloromethane (3*20 mL), dry with anhydrous magnesium sulfate, filter, and separate by column chromatography (dichloromethane:methanol=10:1). The pure target pesticide compound 4d is obtained, and the structural formula is shown in FIG. 2, wherein R is ethyl.

Embodiment 9

The invention relates to a process method for producing an insecticide by using carbon dioxide, wherein the insecticide is compound 3e, and the preparation process comprises the following steps:

1) Weighing 1 mmol of 1,3-cyclohexanedione compound 1e, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 50° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1, 3-cyclohexanedione compound 2e is obtained.

4) Weigh 1 mmol of 2-carboxyl-1,3-cyclohexanedione compound 2e into around bottom flask, add 10 mL of tetrahydrofuran, add 2.2 times equivalent of thionyl chloride, add a drop of DMF, heat to 65° C. and stir for 1 h. After the reaction, it was cooled to room temperature, the solvent was removed under reduced pressure, and dissolved in 10 mL of dichloromethane solution.

5) Dissolve 2 times equivalent of aniline in 1 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3e is obtained, and the structural formula is shown in FIG. 1.

Embodiment 10

The invention relates to a process method for producing an insecticide by using carbon dioxide, wherein the insecticide is compound 4e, and the preparation process comprises the following steps:

1) Weigh 3e 100 mg of the compound prepared in embodiment 1 into a round bottom flask, add 6 mL of 50% sulfuric acid, heat to 80° C. and stir for 12 h.

2) After completion of the reaction, cool to room temperature, add 50 mL of water to the reaction solution, extract with dichloromethane (3*20 mL), dry with anhydrous magnesium sulfate, filter, and separate by column chromatography (dichloromethane:methanol=10:1). The pure target pesticide compound 4e is obtained, and the structural formula is shown in FIG. 2, wherein R is propyl.

Embodiment 11

The invention relates to a process method for producing an insecticide by using carbon dioxide, wherein the insecticide is compound 3(3a-3e), and the preparation process comprises the following steps:

1) Weighing 1 mmol of 1,3-cyclohexanedione compound 1a, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 55° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1, 3-cyclohexanedione compound 2a is obtained.

4) Weigh 1 mmol of 2-carboxyl-1,3-cyclohexanedione compound 2a into around bottom flask, add 10 mL of tetrahydrofuran, add 2.2 times equivalent of thionyl chloride, add a drop of DMF, heat to 65° C. and stir for 2 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 3 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3a is obtained, and the structural formula is shown in FIG. 1.

Embodiment 12

The invention relates to a process method for producing an insecticide by using carbon dioxide, wherein the insecticide is compound 3b, and the preparation process comprises the following steps:

1) Weighing 1 mmol of 1,3-cyclohexanedione compound 1b, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 55° C. and stirring for 48 hours.

2) After stirring was completed, 50 mL of diethyl ether was added to the reacted mixture and filtered.

3) Column chromatography separation (ethyl acetate: petroleum ether=3:1); the pure target product 2-carboxyl-1, 3-cyclohexanedione compound 2b is obtained.

4) Weigh 1 mmol of 2-carboxyl-1,3-cyclohexanedione compound 2b into a round bottom flask, add 10 mL of tetrahydrofuran, add 2.2 times equivalent of thionyl chloride, add a drop of DMF, heat to 65° C. and stir for 2 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3b is obtained, and the structural formula is shown in FIG. 1.

Embodiment 13

The invention relates to a process method for producing an insecticide by using carbon dioxide, wherein the insecticide is compound 3c, and the preparation process comprises the following steps:

1) Weighing 1 mmol of 1,3-cyclohexanedione compound 1c, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N,N-dimethylformamide, heating to 55° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2c is obtained.

4) Weigh 1 mmol of 2-carboxyl-1,3-cyclohexanedione compound 2c into a round bottom flask, add 10 mL of tetrahydrofuran, add 2.2 times equivalent of thionyl chloride, add a drop of DMF, heat to 65° C. and stir for 2 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3c is obtained, and the structural formula is shown in FIG. 1.

Embodiment 14

The invention relates to a process method for producing an insecticide by using carbon dioxide, wherein the insecticide is compound 3d, and the preparation process comprises the following steps:

1) Weighing 1 mmol of 1,3-cyclohexanedione compound 1d, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 55° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2d is obtained.

4) Weigh 1 mmol of 2-carboxyl-1,3-cyclohexanedione compound 2d into a round bottom flask, add 10 mL of tetrahydrofuran, add 2.2 times equivalent of thionyl chloride, add a drop of DMF, heat to 65° C. and stir for 2 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3d is obtained, and the structural formula is shown in FIG. 1.

Embodiment 15

The invention relates to a process method for producing an insecticide by using carbon dioxide, wherein the insecticide is compound 3e, and the preparation process comprises the following steps:

1) Weighing 1 mmol of 1,3-cyclohexanedione compound 1e, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N,N-dimethylformamide, heating to 55° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2e is obtained.

4) Weigh 1 mmol of 2-carboxyl-1,3-cyclohexanedione compound 2e into a round bottom flask, add 10 mL of tetrahydrofuran, add 2.2 times equivalent of thionyl chloride, add a drop of DMF, heat to 65° C. and stir for 2 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3e is obtained, and the structural formula is shown in FIG. 1.

Embodiment 16

The invention relates to a process method for producing an insecticide by using carbon dioxide, wherein the insecticide is compound 3(3a-3e), and the preparation process comprises the following steps:

1) Weighing 1 mmol of 1,3-cyclohexanedione compound 1a, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 60° C. and stirring for 36 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2a is obtained.

4) Weigh 1 mmol of 2-carboxyl-1,3-cyclohexanedione compound 2a into around bottom flask, add 10 mL of tetrahydrofuran, add 2.2 times equivalent of thionyl chloride, add a drop of DMF, heat to 65° C. and stir for 1.5 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2.5 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3a is obtained, and the structural formula is shown in FIG. 1.

Embodiment 17

The invention relates to a process method for producing an insecticide by using carbon dioxide, wherein the insecticide is compound 3b, and the preparation process comprises the following steps:

1) Weighing 1 mmol of 1,3-cyclohexanedione compound 1b, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 60° C. and stirring for 36 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2b is obtained.

4) Weigh 1 mmol of 2-carboxyl-1,3-cyclohexanedione compound 2b into a round bottom flask, add 10 mL of tetrahydrofuran, add 2.2 times equivalent of thionyl chloride, add a drop of DMF, heat to 65° C. and stir for 1 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3b is obtained, and the structural formula is shown in FIG. 1.

Embodiment 18

The invention relates to a process method for producing an insecticide by using carbon dioxide, wherein the insecticide is compound 3c, and the preparation process comprises the following steps:

1) Weighing 1 mmol of 1,3-cyclohexanedione compound 1c, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 60° C. and stirring for 40 hours.

2) After stirring was completed, 50 mL of diethyl ether was added to the reacted mixture and filtered.

3) Column chromatography separation (ethyl acetate: petroleum ether=3:1); the pure target product 2-carboxyl-1, 3-cyclohexanedione compound 2c is obtained.

4) Weigh 1 mmol of 2-carboxyl-1,3-cyclohexanedione compound 2c into around bottom flask, add 10 mL of tetrahydrofuran, add 2.2 times equivalent of thionyl chloride, add a drop of DMF, heat to 65° C. and stir for 1.5 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 3 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3c is obtained, and the structural formula is shown in FIG. 1.

Embodiment 19

The invention relates to a process method for producing an insecticide by using carbon dioxide, wherein the insecticide is compound 3d, and the preparation process comprises the following steps:

1) Weighing 1 mmol of 1,3-cyclohexanedione compound 1d, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 60° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1,3-cyclohexanedione compound 2d is obtained.

4) Weigh 1 mmol of 2-carboxyl-1,3-cyclohexanedione compound 2d into a round bottom flask, add 10 mL of tetrahydrofuran, add 2.2 times equivalent of thionyl chloride, add a drop of DMF, heat to 65° C. and stir for 1 h. After the reaction, it was cooled to room temperature, the solvent was removed under reduced pressure, and dissolved in 10 mL of dichloromethane solution.

5) Dissolve 2 times equivalent of aniline in 10 mL of dichloromethane, drop the dichloromethane solution obtained in step 4) into the dichloromethane solution containing aniline, and react for 2 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3d is obtained, and the structural formula is shown in FIG. 1.

Embodiment 20

The invention relates to a process method for producing an insecticide by using carbon dioxide, wherein the insecticide is compound 3e, and the preparation process comprises the following steps:

1) Weighing 1 mmol of 1,3-cyclohexanedione compound 1e, 1 0.5 mmol of cesium carbonate and 0.1 mmol of cuprous iodide into a Schlenk bottle, vacuumizing the Schlenk bottle, introducing carbon dioxide (balloon), adding 5 mL of anhydrous N, N-dimethylformamide, heating to 60° C. and stirring for 48 hours.

2) After stirring was completed, 50 mL of diethyl ether was added to the reacted mixture and filtered.

3) Dissolve the filter residue in 10 mL of water, adjust the pH to 1, extract with dichloromethane (3*20 mL), dry with anhydrous magnesium sulfate, filter, and separate by column chromatography (ethyl acetate:petroleum ether=3:1); The pure target product 2-carboxyl-1, 3-cyclohexanedione compound 2e is obtained.

4) Weigh 1 mmol of 2-carboxyl-1,3-cyclohexanedione compound 2e into around bottom flask, add 10 mL of tetrahydrofuran, add 2.2 times equivalent of thionyl chloride, add a drop of DMF, heat to 65° C. and stir for 1.5 h. After the reaction, it was cooled to room temperature, the solvent was removed under reduced pressure, and dissolved in 10 mL of dichloromethane solution.

5) Dissolve 2 times equivalent of aniline in 10 mL of methylene chloride, drop the methylene chloride solution obtained in step 4) into the methylene chloride solution containing aniline, and react for 2.5 h at normal temperature.

6) After the reaction is completed, the solvent is removed under reduced pressure, 50 mL of water is added to the residue, dichloromethane is extracted (3*20 mL), anhydrous magnesium sulfate is dried, filtered and separated by column chromatography (ethyl acetate:petroleum ether=1:3). The pure target pesticide compound 3e is obtained, and the structural formula is shown in FIG. 1.

Test Method for Pesticide Activity:

Note: Since 4(4a-4e) is a class of compounds with insecticidal activity that have been reported, the insecticidal activity of 4 is not continuously tested, and only 3(3a-3e) is tested.

1) Activity of killing *Mythimna separata* Walker: *Mythimna separata* Walker, a normal population raised indoors. In the leaf dipping method, corn leaves are dipped in a liquid medicine (600 GML$^{-1}$) prepared by acetone, and the 4th instar larvae are inoculated after the liquid medicine, mainly for stomach toxicity and contact killing, and the feeding phenomenon of the larvae is observed. Mortality was examined 24 hours. The mortality rate is shown in table 1.

2) Activity of killing *Culexpipiens pallens* larval: *Culicides pallens*, a normal indoor population. Weigh about 5 mg of the test compound into a penicillin vial, add 5 mL of acetone (or a suitable solvent), and shake to dissolve, i.e. 1000 μg·ml$^{-1}$ mother liquor. 0.5 mL mother liquor was removed and added into a 100 mL beaker containing 39.9 mL of water. Ten 4th instar mosquito larvae were selected and poured into the beaker together with 10 mL of feeding liquid. The concentration of the liquid medicine was 10 μg·ml$^{-1}$. Place the treatment in the standard treatment room, and check the results 24 h. The blank control was an aqueous solution containing 0.5 mL of test solvent. The mortality rate is shown in table 1.

3) Activity of killing *Helicoverpa armigera:Helicoverpa armigera*, a normal population raised indoors. Test method: leaf soaking method. In the leaf soaking method, corn leaves are soaked in a liquid medicine prepared by acetone (600 ppm, 600 mg/L), ground and put into 24 holes after the liquid medicine is dried, one third-instar larva is inserted into each hole, 10 are used for each time, and three times are repeated, a total of 30 test insects are tested, mainly gastric toxicity and contact killing effects, and the feeding phenomenon of the larva is observed. Mortality was examined 72 hours later. The mortality rate is shown in table 1.

4) Activity of killing *Ostrinia nubilalis* Hubner: *Ostrinia nubilalis* Hubner, a normal population raised indoors. Test method: leaf soaking method. In the leaf dipping method, corn leaves are dipped in a liquid medicine prepared by acetone (200 ppm, 200 mg/L), 10 3rd instar larvae are inoculated into a culture dish after the liquid medicine is dried, and 30 test larvae are shared for three times, mainly gastric toxicity and contact killing effects, and the feeding phenomenon of the larvae is observed. Mortality was examined 72 hours later. The mortality rate is shown in table 1.

TABLE 1

| Entry | Mythimna separata walker | | Culex pipiens pallens | |
|---|---|---|---|---|
| | Concentration | Mortality | Concentration | Mortality |
| 3a | 600(ppm) | 100% | 10(ppm) | 20% |
| 3b | 600(ppm) | 35% | 10(ppm) | 70% |
| 3c | 600(ppm) | 30% | 10(ppm) | 80% |
| 3d | 200(ppm) | 100% | 10(ppm) | 20% |
| 3e | 600(ppm) | 55% | 10(ppm) | 100% |

| Entry | Helicoverpa armigera | | Ostrinia nubilalis hubner | |
|---|---|---|---|---|
| | Concentration | Mortality | Concentration | Mortality |
| 3a | 600(ppm) | 75% | 600(ppm) | 70% |
| 3b | 600(ppm) | 15% | 600(ppm) | 20% |
| 3c | 600(ppm) | 10% | 600(ppm) | 15% |
| 3d | 600(ppm) | 100% | 600(ppm) | 100% |
| 3e | 600(ppm) | 25% | 600(ppm) | 30% |

The invention claimed is:

1. A process method for producing a pesticide by using carbon dioxide, comprising the following steps:

1) Weighing a 1,3-cyclohexanedione substrate, a monovalent copper salt catalyst and cesium carbonate in a Schlenk bottle; vacuumizing the Schlenk bottle and introducing carbon dioxide to fill the Schlenk bottle with carbon dioxide gas; then injecting an anhydrous N, N-dimethylformanide (DMF) solvent into the Schlenk bottle, placing the Schlenk bottle into an oil bath set at a temperature of between 50-60° C., and leaving the mixture in the Schlenk bottle to react for 36-48 h; wherein the dosage ratio of 1,3-cyclohexanedione substrate:cesium carbonate:monovalent copper salt catalyst:solvent is 1 mmol: 1.5 mmol: 0.1 mmol: 5 mL;

2) After the reaction is completed, acidifying the resulting mixture with hydrochloric acid, extracting the acidified mixture, and then passing the extracted mixture through a silica gel column to obtain a pure intermediate 2-carboxyl-1,3-cyclohexanedione compound, wherein the recovery yield is at least 80%;

3) Adding the 2-carboxyl-1,3-cyclohexanedione compound obtained in step 2), thionyl chloride, a tetrahydrofuran solvent and a drop of DMF into a round bottom flask, reacting for 1-2 h in an oil bath at 65° C., and removing the solvent from the resulting mixture in the round bottom flask under reduced pressure to obtain an oily yellow liquid, wherein the dosage ratio of the 2-carboxyl-1,3-cyclohexanedione compound:thionyl chloride:tetrahydrofuran solvent is 1 mmol: 2.2 mmol: 10 mL;

4) dropping the oily yellow liquid obtained in step 3) into a dichloromethane solution containing aniline, reacting for 2-3 h at room temperature, obtaining a crude product after the reaction, and separating the crude product by column chromatography to obtain a pesticide compound;

wherein the 1,3-cyclohexanedione substrate has the following structural formula 1(a-e) in the following preparation route 1, the 2-carboxyl-1,3-cyclohexanedione compound has the following structural formula 2(a-e), and the pesticide compound has the following structural formula 3(a-e);

preparation route 1

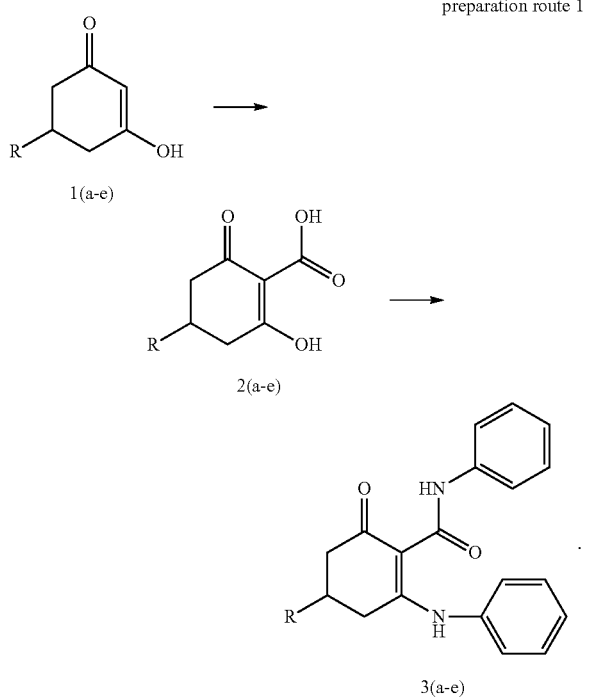

where R is one selected from the group consisting of hydrogen, methyl, dimethyl, ethyl and propyl.

2. The process method according to claim 1, characterized in that the process method further comprises the following steps:
   5) the pesticide compound obtained in claim 1 is added into concentrated sulfuric acid with a mass concentration of 50% and refluxed at 80° C. for 12 h to produce a crude product which is then purified using a silica gel column to produce a pure pesticide product compound;

wherein the pesticide product compound produced in step 5) has the following structural formula 4(a-e) in the following preparation route 2;

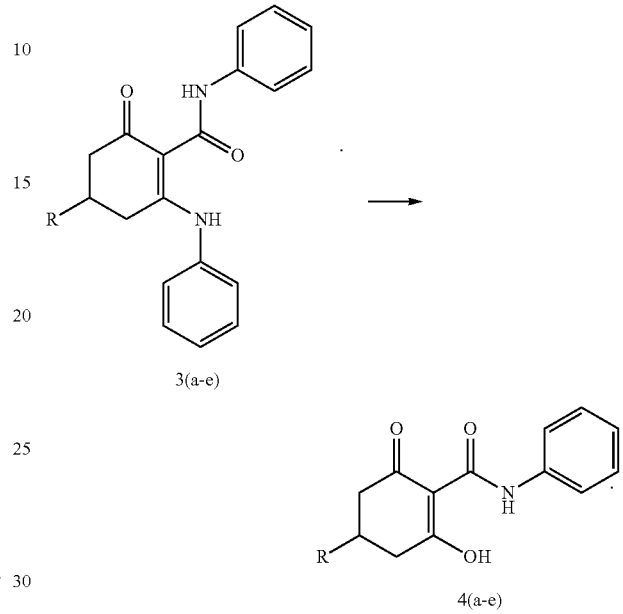

3. The process method according to claim 1, characterized in that the monovalent copper salt catalyst is cuprous iodide, cuprous bromide or cuprous oxide.

* * * * *